United States Patent
Katayama (10) Patent No.: US 12,383,123 B2
(45) Date of Patent: Aug. 12, 2025

(54) ENDOSCOPE HAVING A JOINING PORTION IN WHICH LIQUID AND GAS JOIN

(71) Applicant: HOYA CORPORATION, Tokyo (JP)

(72) Inventor: Toshiyuki Katayama, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 397 days.

(21) Appl. No.: 18/012,008

(22) PCT Filed: Sep. 17, 2021

(86) PCT No.: PCT/JP2021/034268
§ 371 (c)(1),
(2) Date: Dec. 21, 2022

(87) PCT Pub. No.: WO2022/070982
PCT Pub. Date: Apr. 7, 2022

(65) Prior Publication Data
US 2023/0263377 A1    Aug. 24, 2023

(30) Foreign Application Priority Data
Oct. 2, 2020 (JP) .................................. 2020-167753

(51) Int. Cl.
*A61B 1/015* (2006.01)
*A61B 1/00* (2006.01)

(52) U.S. Cl.
CPC .......... *A61B 1/015* (2013.01); *A61B 1/00119* (2013.01); *A61B 1/00128* (2013.01)

(58) Field of Classification Search
CPC ..... A61B 1/015; A61B 1/012; A61B 1/00119; A61B 1/00128; A61B 1/00091
(Continued)

(56) References Cited

U.S. PATENT DOCUMENTS 5,733,243 A * 3/1998 Yabe ...................... A61B 1/012
600/156
6,702,738 B2    3/2004 Ito
(Continued)

FOREIGN PATENT DOCUMENTS

JP      11-253393 A      9/1999
JP      3017754 B2 *     3/2000
(Continued)

OTHER PUBLICATIONS

Machine language translation of JP2010046300 (Year: 2010).*
(Continued)

*Primary Examiner* — John P Leubecker
(74) *Attorney, Agent, or Firm* — GREENBLUM & BERNSTEIN, P.L.C.

(57) ABSTRACT

An endoscope capable of preventing a liquid in a liquid path from being sucked up and injected together with a gas at the time of an air supply operation. In an endoscope including a liquid path through which a liquid passes and a gas path through which a gas passes, and in which a joining recessed portion in which the liquid and the gas join is formed in a distal end portion, one end side of the liquid path and one end side of the gas path communicate with the joining recessed portion, and a size of a first communication hole between the gas path and the joining recessed portion is made larger than a size of a second communication hole between the liquid path and the joining recessed portion.

7 Claims, 10 Drawing Sheets

(58) Field of Classification Search
USPC .................................................. 600/156, 159
See application file for complete search history.

(56) References Cited

U.S. PATENT DOCUMENTS

| | | | |
|---|---|---|---|
| 6,764,442 | B2 | 7/2004 | Ota et al. |
| 2002/0040181 | A1 | 4/2002 | Arai et al. |
| 2009/0253964 | A1 | 10/2009 | Miyamoto |
| 2011/0319716 | A1* | 12/2011 | Naito ..................... A61B 1/015 |
| | | | 600/157 |
| 2012/0316395 | A1 | 12/2012 | Koga |

FOREIGN PATENT DOCUMENTS

| JP | 2001-258824 A | 9/2001 |
|---|---|---|
| JP | 2002-102154 A | 4/2002 |
| JP | 2005-000567 A | 1/2005 |
| JP | 2007-190118 A | 8/2007 |
| JP | 2010-46300 A | 3/2010 |
| JP | 2012-254153 A | 12/2012 |
| JP | 2013-172773 A | 9/2013 |
| JP | 2013-236678 A | 11/2013 |

OTHER PUBLICATIONS

European Search Report issued in EP Patent Application No. 21875284.8, dated Jun. 19, 2024.
International Search Report issued in International Bureau of WIPO Patent Application No. PCT/JP2021/034268, dated Oct. 19, 2021, along with an English translation thereof.
First Office Action issued in Chinese Patent Application No. 202180043168.9, dated Apr. 18, 2025, along with an English translation thereof.

* cited by examiner

ENDOSCOPE HAVING A JOINING PORTION IN WHICH LIQUID AND GAS JOIN

TECHNICAL FIELD

The present invention relates to an endoscope in which a joining recessed portion in which a liquid and a gas join is formed in a distal end portion.

The present application claims priority based on Japanese Patent Application No. 2020-167753 filed on Oct. 2, 2020, the entire contents of which are incorporated herein by reference.

BACKGROUND ART

Conventionally, an endoscope having a gas path and a liquid path and in which distal ends of the gas path and the liquid path communicate with each other in a distal end portion of an insertion portion to be inserted into a body cavity has been widely used.

For example, Patent Literature 1 discloses an endoscope in which the size of an opening of an air supply passage pipe (gas path) is made smaller than the size of an opening of a nozzle that injects air or water at a communication portion between the air supply passage pipe and a water supply passage pipe (liquid path), whereby water does not flow back into the air supply passage pipe side at the time of a water supply operation, and water droplets can be suppressed from being ejected together with air at the time of a subsequent air supply operation.

CITATION LIST

Patent Literature

Patent Literature 1: JP 2007-190118 A

SUMMARY OF INVENTION

Technical Problem

Meanwhile, in an endoscope in which a joining recessed portion in which a liquid and a gas join is formed in a distal end portion of an insertion portion, and the liquid or the gas flows to a nozzle via the joining recessed portion, there may be a problem that the liquid in a liquid path is sucked up due to a pressure difference between the inside of the joining recessed portion and the inside of the liquid path and is injected through the nozzle together with the gas at the time of an air supply operation of injecting only the gas through the nozzle.

However, the endoscope of Patent Literature 1 does not consider such a problem and cannot solve the problem.

The present invention has been made in view of such circumstances, and an object thereof is to provide an endoscope capable of preventing a liquid in a liquid path from being sucked up and injected together with a gas at the time of an air supply operation.

Solution to Problem

An endoscope according to the present invention includes a liquid path through which a liquid passes and a gas path through which a gas passes, and in which a joining recessed portion in which the liquid and the gas join is formed in a distal end portion. One end side of the liquid path and one end side of the gas path communicate with the joining recessed portion, and a size of a first communication hole between the gas path and the joining recessed portion is larger than a size of a second communication hole between the liquid path and the joining recessed portion.

In the present invention, since the size of the first communication hole between the gas path and the joining recessed portion is larger than the size of the second communication hole between the liquid path and the joining recessed portion, an increase in speed of air in a vicinity of the first communication hole is suppressed and the liquid in the liquid path is prevented from being sucked up in the case of the air supply operation of injecting only the gas through the nozzle.

Advantageous Effects of Invention

According to the present invention, a liquid in a liquid path can be prevented from being sucked up and injected together with a gas at the time of an air supply operation.

DESCRIPTION OF EMBODIMENTS

Hereinafter, an endoscope according to embodiments of the present invention will be described in detail with reference to the drawings.

First Embodiment

Figure 1:
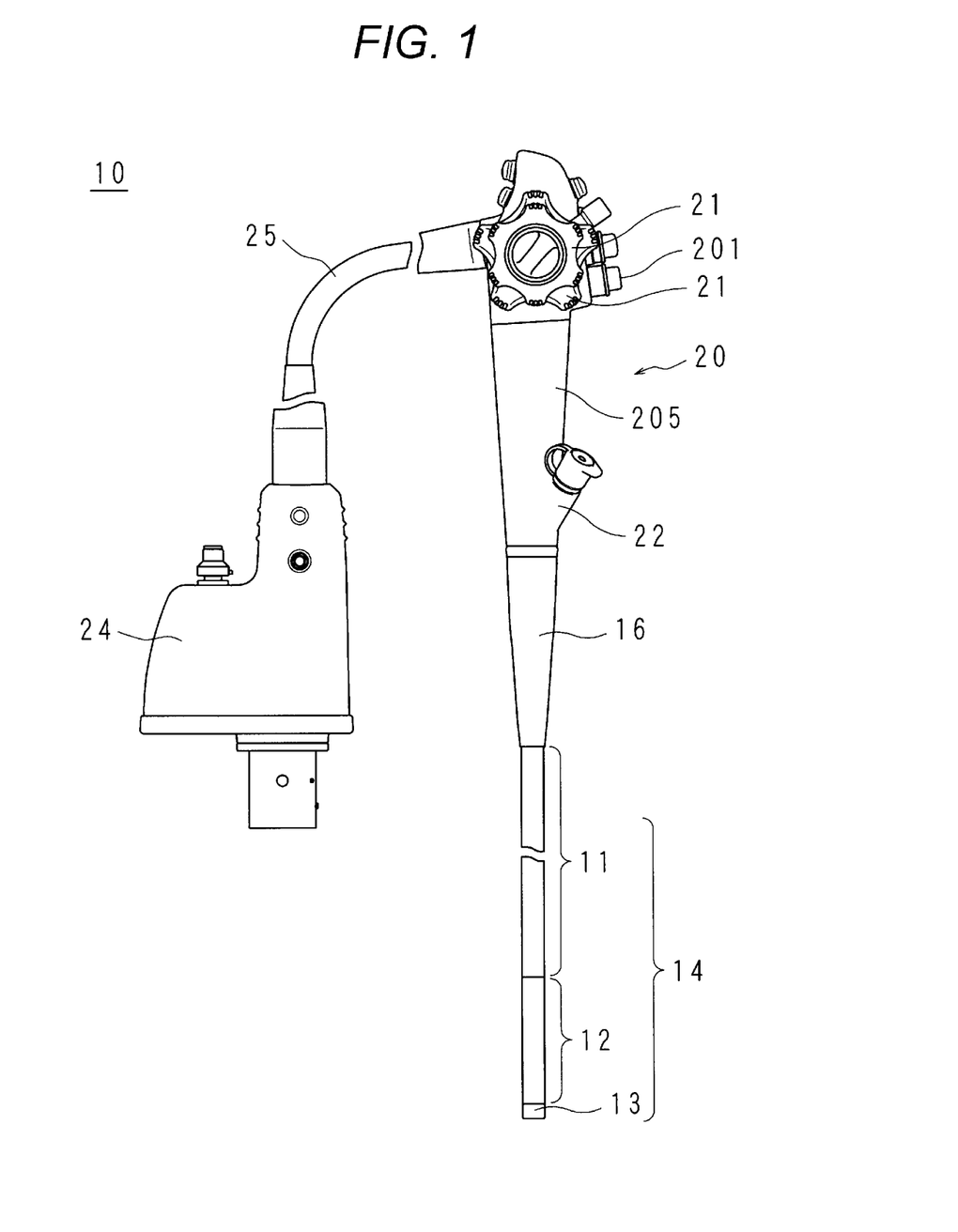
FIG. 1 is an external view of an endoscope according to a first embodiment of the present invention.

FIG. 1 is an external view of an endoscope 10 according to a first embodiment of the present invention. The endoscope 10 according to the present embodiment includes an imaging means, and is provided with an insertion portion 14 to be inserted into a body cavity of a subject, an operation unit 20 for operating the insertion portion 14, and a connector unit 24 connected with a processor, a light source device, an air supply/water supply device, and the like, which are not illustrated.

The insertion portion 14 is connected with the operation unit 20 via a bend preventing portion 16, and the operation unit 20 is connected with the connector unit 24 via a universal cord 25.

The universal cord 25 has pliability, and includes an electric line that sends an electric signal from an imaging means of the insertion portion 14 to the connector unit 24, and a water passage through which water passes and an air passage through which air passes, which are sent from the connector unit 24.

The operation unit 20 includes a grip portion 205, buttons 201 each for receiving an instruction such as water feed or air feed from the user, and a bending knob 21 for operating bending of a bending section 12 to be described below.

The grip portion 205 has a substantially cylindrical shape, and is reduced in diameter toward the insertion portion 14. The grip portion 205 is provided with a channel inlet 22, into which a treatment tool or the like is to be inserted, near the insertion portion 14 side.

The insertion portion 14 has a cylindrical shape with a small diameter, and is configured to be bendable. A distal end portion 13, a bending section 12, and a soft portion 11 are provided in this order from one end of the distal end side. The bending section 12 is bent according to an operation of the bending knob 21.

The distal end portion 13 has a columnar shape, and accommodates an imaging unit (not illustrated) including an imaging means such as a charge coupled device (CCD) or a complementary metal oxide semiconductor (CMOS), an observation optical system, and the like.

Figure 2:
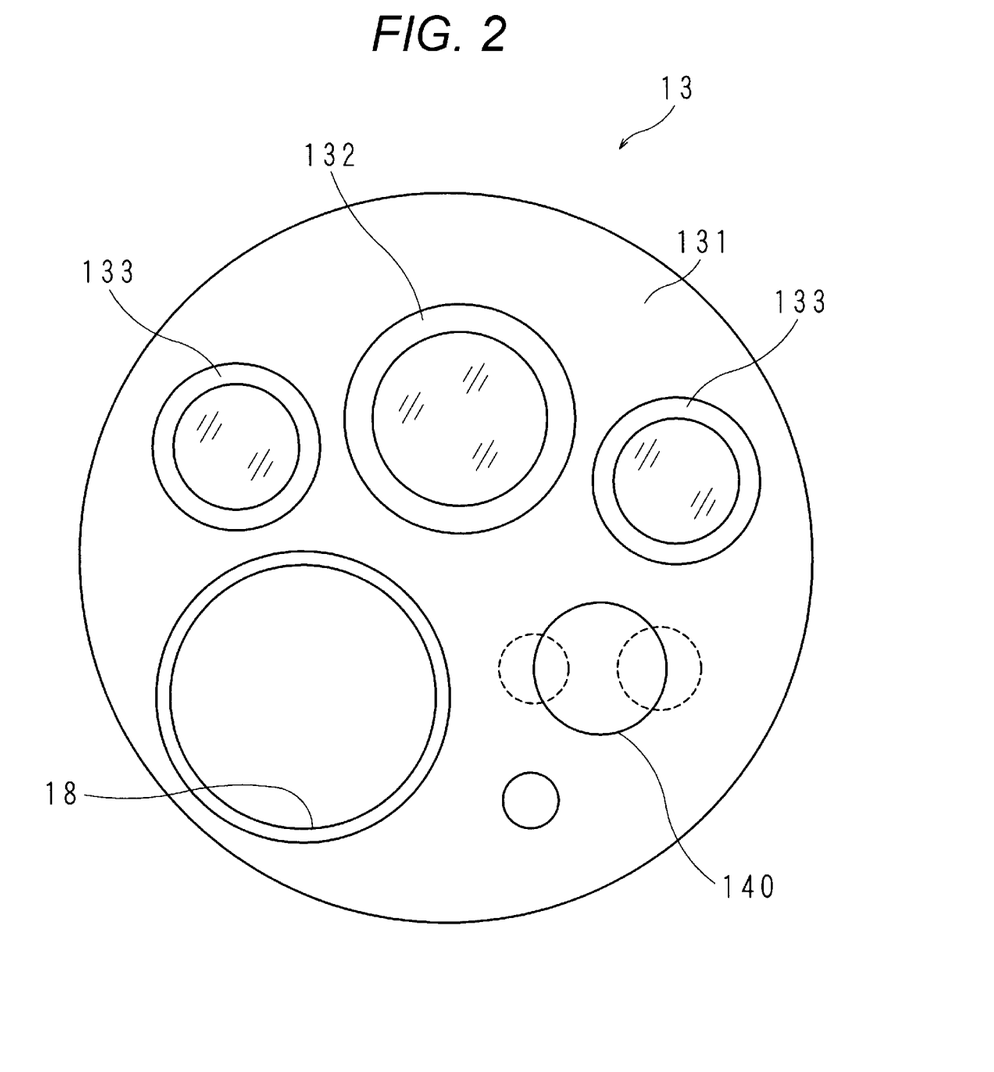
FIG. 2 is a schematic view illustrating a distal end surface of a distal end portion of the endoscope.

FIG. 2 is a schematic view illustrating a distal end surface 131 of the distal end portion 13 of the endoscope 10. The distal end surface 131 of the distal end portion 13 has a circular shape. The distal end portion 13 is provided with an observation optical system 132, an air supply/water supply nozzle 140, a channel outlet 18, an illumination optical system 133, and the like.

Two illumination optical systems 133 are provided on the distal end surface 131 in a separated manner from each other, and the observation optical system 132 is provided between the two illumination optical systems 133. Further, the air supply/water supply nozzle 140 and the channel outlet 18 are provided at a distance from the observation optical system 132 in the distal end surface 131. The air supply/water supply nozzle 140 injects air or water toward the observation optical system 132, and the illumination optical system 133 emits irradiation light to illuminate an object.

Figure 3:
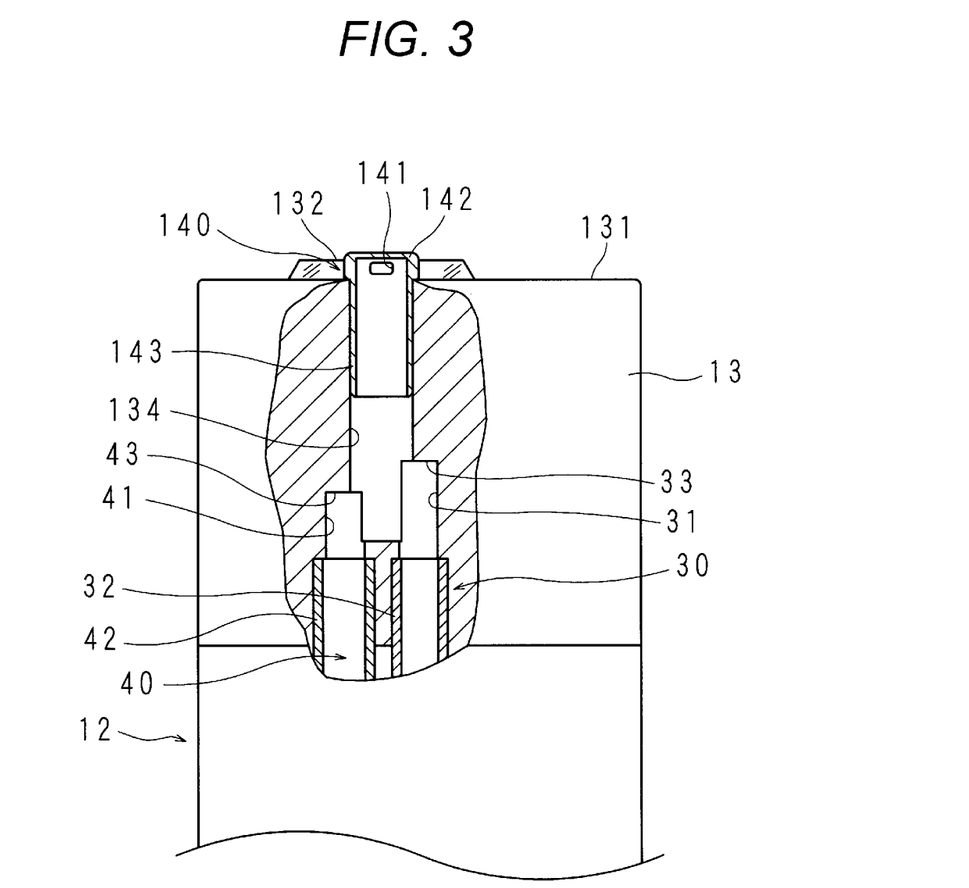
FIG. 3 is a partial cross-sectional view for describing a configuration of the distal end portion.

FIG. 3 is a schematic cross-sectional view for describing a configuration of the distal end portion 13.

A joining recessed portion 134 in which air and water sent from the operation unit 20 join is formed in the distal end surface 131 of the distal end portion 13, and a part of the air supply/water supply nozzle 140 is engaged with the joining recessed portion 134.

The joining recessed portion 134 has a circular shape in cross-sectional view and extends in an axial length direction of the distal end portion 13. One end side of the joining recessed portion 134, the one end side being closer to the distal end surface 131 in a longitudinal direction, is engaged with the air supply/water supply nozzle 140. Further, the other end side of the joining recessed portion 134 communicates with a gas path 30 and a liquid path 40 to be described below.

The air supply/water supply nozzle 140 includes a cylindrical portion 143 having a circular shape in cross-sectional view, and a lid portion 142 that covers an opening end on one end side of the cylindrical portion 143. The lid portion 142 and the cylindrical portion 143 are integrally formed. The cylindrical portion 143 has an outer diameter slightly smaller than an inner diameter of the joining recessed portion 134, and most of the cylindrical portion is internally fitted into the joining recessed portion 134. The lid portion 142 has a disk shape and has a diameter larger than the outer diameter of the cylindrical portion 143. In a state where the air supply/water supply nozzle 140 is engaged with the joining recessed portion 134, only the lid portion 142 is exposed on the distal end surface 131.

Further, the air supply/water supply nozzle 140 has an outlet 141 through which air or water is emitted. The outlet 141 has a substantially oval shape and opens toward the observation optical system 132. The outlet 141 is provided on the lid portion 142 side in the cylindrical portion 143.

As described above, the other end side of the joining recessed portion 134 communicates with the gas path 30 and the liquid path 40. The gas path 30 supplies a gas (for example, air) sent from the air supply/water supply device to the air supply/water supply nozzle 140. Further, the liquid path 40 supplies a liquid (for example, water) sent from the air supply/water supply device to the air supply/water supply nozzle 140.

The gas path 30 includes an air supply tube 32 and an air supply connection portion 31. The air supply tube 32 communicates with the other end side of the joining recessed portion 134 via the air supply connection portion 31. Further, the air supply tube 32 penetrates the insertion portion 14 in the longitudinal direction, and is provided so as to straddle the bending section 12 and the distal end portion 13. That is, one end of the air supply tube 32 is connected to the air supply connection portion 31, and the other end of the air supply tube 32 is connected to the air supply/water supply device through the operation unit 20 and the connector unit 24.

Further, the liquid path 40 includes a water supply tube 42 and a water supply connection portion 41. The water supply tube 42 communicates with the other end side of the joining recessed portion 134 via the water supply connection portion 41. Further, the water supply tube 42 penetrates the insertion portion 14 in the longitudinal direction, and is provided so as to straddle the bending section 12 and the distal end portion 13. That is, one end of the water supply tube 42 is connected to the water supply connection portion 41, and the other end of the water supply tube 42 is connected to the air supply/water supply device through the operation unit 20 and the connector unit 24.

Figure 4:
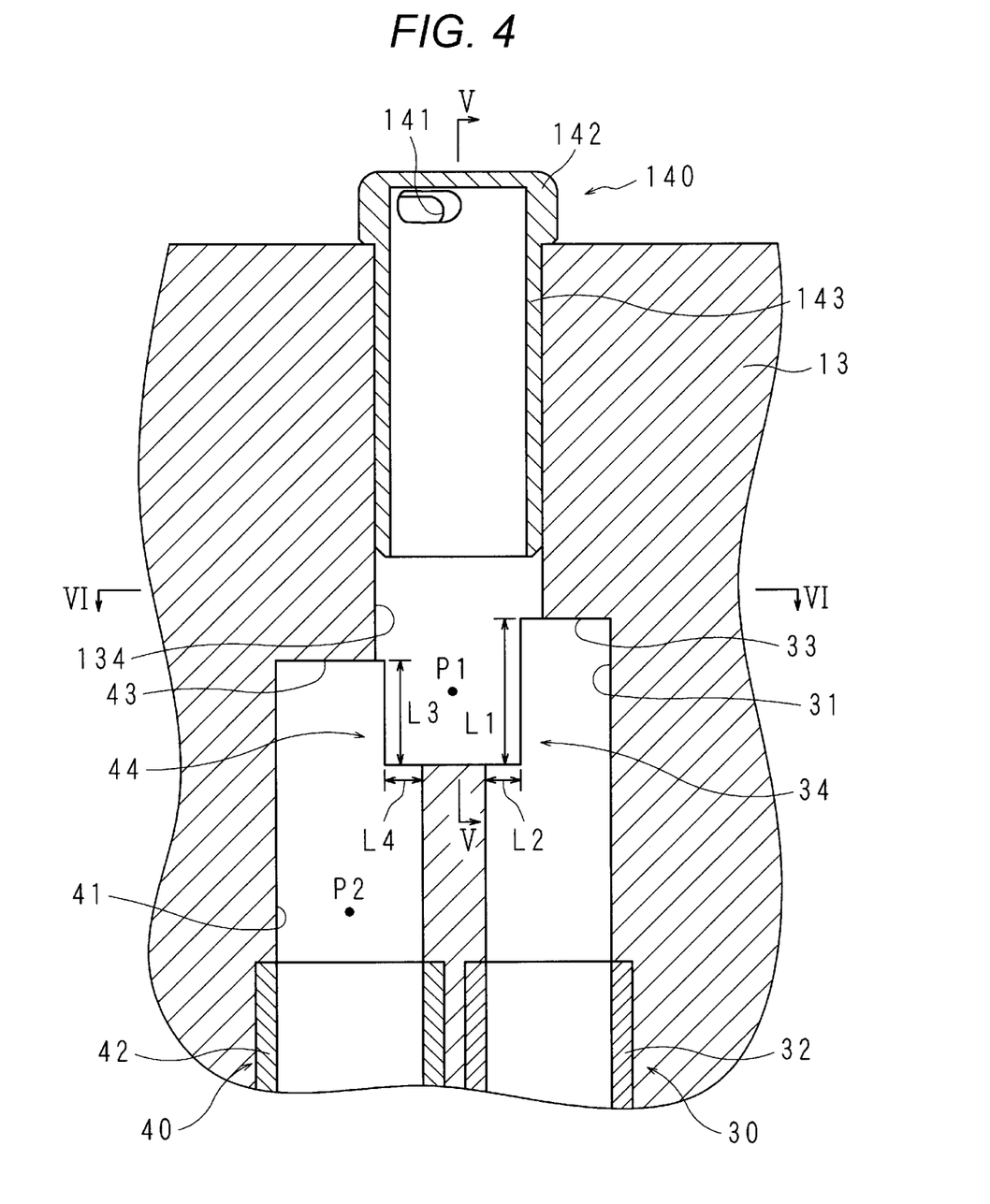
FIG. 4 is an enlarged view illustrating a portion of a joining recessed portion in FIG. 3 in an enlarged manner.
Figure 5:
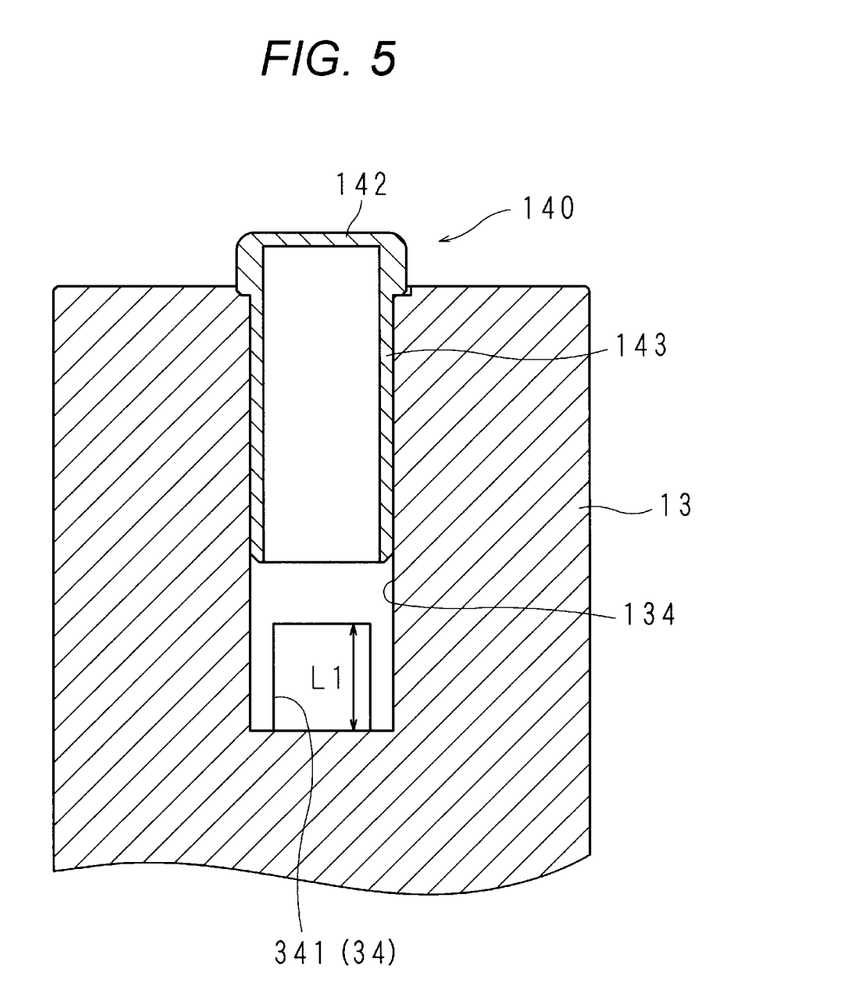
FIG. 5 is a cross-sectional view taken along line V-V of FIG. 4.
Figure 6:
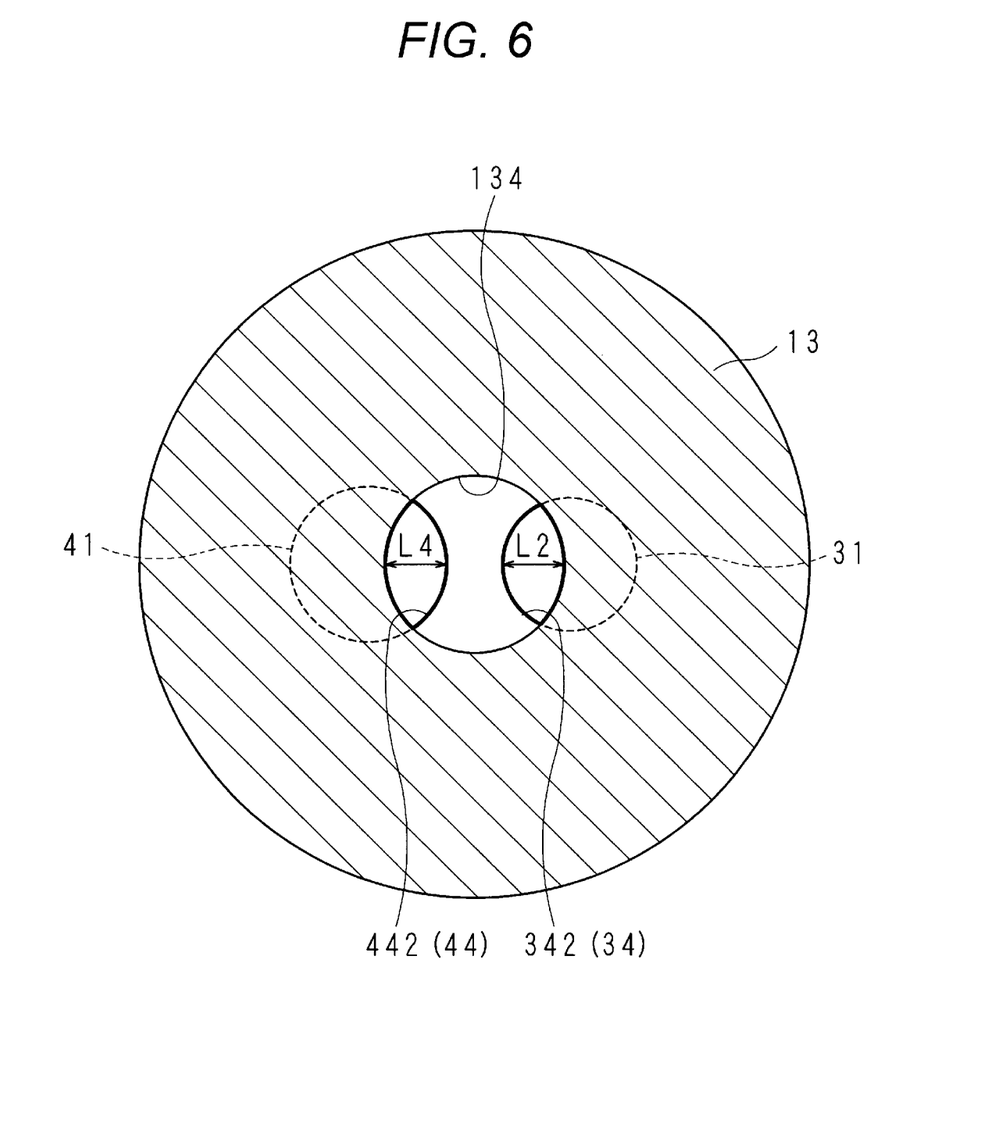
FIG. 6 is a cross-sectional view taken along line VI-VI of FIG. 4.
Figure 7:
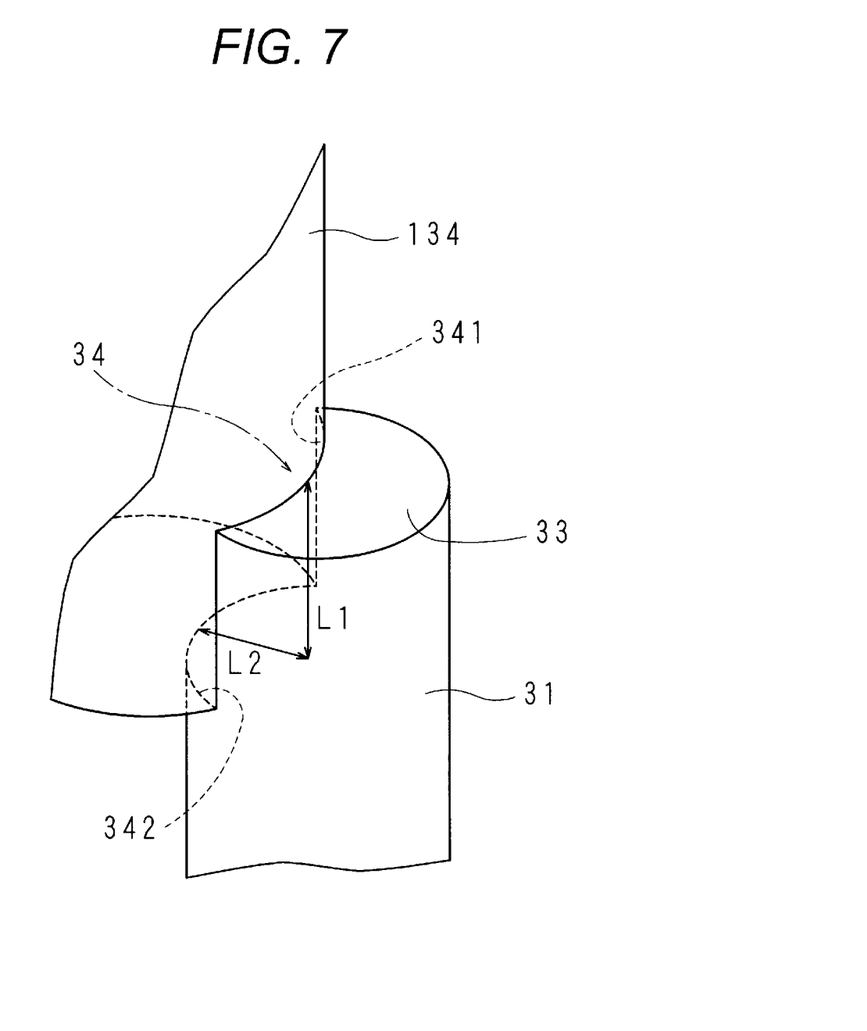
FIG. 7 is an explanatory view for describing a communication state between the joining recessed portion and an air supply connection portion.

FIG. 4 is an enlarged view illustrating a portion of the joining recessed portion 134 in FIG. 3 in an enlarged manner, FIG. 5 is a cross-sectional view taken along line V-V of FIG. 4, FIG. 6 is a cross-sectional view taken along line VI-VI of FIG. 4, and FIG. 7 is an explanatory view for describing a communication state between the joining recessed portion 134 and an air supply connection portion 31. FIG. 7 illustrates outlines of the joining recessed portion 134 and the air supply connection portion 31.

The air supply connection portion 31 has a substantially cylindrical shape and sends air flowing through the air supply tube 32 to the joining recessed portion 134. The air supply connection portion 31 has a diameter equal to the inner diameter of the air supply tube 32, and an upstream end thereof is connected to the air supply tube 32. Further, in the air supply connection portion 31, a gas guide wall 33 for guiding the air into the joining recessed portion 134 is formed at a downstream end. The gas guide wall 33 is formed so as to be orthogonal to the axial length direction of the air supply connection portion 31.

A first communication hole 34 is formed in a communication portion between the air supply connection portion 31 and the joining recessed portion 134. In the first communication hole 34, a dimension L1 in the axial length direction of the air supply connection portion 31 is longer than a dimension L2 in a direction intersecting the axial length direction of the air supply connection portion 31.

That is, the first communication hole 34 includes an orthogonal opening portion 341 (see FIGS. 5 and 7) opening in a direction orthogonal to the axial length direction of the air supply connection portion 31 and a parallel opening portion 342 (see FIGS. 6 and 7) opening in a direction parallel to the axial length direction of the air supply connection portion 31. The orthogonal opening portion 341 is wider than parallel opening portion 342. That is, as described above, since the dimension L1 of the first communication hole 34 is longer than the dimension L2, the orthogonal opening portion 341 is wider than the parallel opening portion 342. The orthogonal opening portion 341 is a region that looks substantially rectangular in FIG. 5, and the parallel opening portion 342 is a region that looks a substantially convex lens in FIG. 6 (see the thick line in FIG. 6).

The water supply connection portion 41 has a substantially cylindrical shape and sends water flowing through the water supply tube 42 to the joining recessed portion 134. The water supply connection portion 41 has a diameter equal to the inner diameter of the water supply tube 42, and an upstream end thereof is connected to the water supply tube 42. In the water supply connection portion 41, a liquid guide wall 43 for guiding the water from the water supply tube 42 into the joining recessed portion 134 is formed at a downstream end. The liquid guide wall 43 is formed so as to be orthogonal to the axial length direction of the water supply connection portion 41.

A second communication hole 44 is formed in a communication portion between the water supply connection portion 41 and the joining recessed portion 134. That is, similarly to the first communication hole 34, the second communication hole 44 includes an orthogonal opening portion (not illustrated) opening in a direction orthogonal to the axial length direction of the water supply connection portion 41 and a parallel opening portion 442 (see FIG. 6) opening in a direction parallel to the axial length direction of the water supply connection portion 41. Similarly to the first communication hole 34, the orthogonal opening portion of the second communication hole 44 is a substantially rectangular region, and the parallel opening portion 442 is a substantially convex lens-shaped region (see the thick line in FIG. 6).

In the second communication hole 44, a dimension L3 in the axial length direction of the water supply connection portion 41 is longer than a dimension L4 in a direction intersecting the axial length direction of the water supply connection portion 41. Meanwhile, the dimension of the water supply connection portion 41 in the axial length direction is shorter than the dimension of the air supply connection portion 31 in the axial length direction (see FIG. 4).

That is, the dimension L3 of the second communication hole 44 is shorter than the dimension L1 of the first communication hole 34 (see FIG. 4), and the dimension L4 of the second communication hole 44 is substantially equal to the dimension L2 of the first communication hole 34 (see FIGS. 4 and 6).

The air sent from the bend preventing portion 16 side via the air supply tube 32 flows into the joining recessed portion 134 via the air supply connection portion 31, and the water sent via the water supply tube 42 flows into the joining recessed portion 134 via the water supply connection portion 41. Thereafter, the air and the water flow into the air supply/water supply nozzle 140 and are emitted toward the observation optical system 132 via the outlet 141.

Meanwhile, in a case of an air supply operation of injecting only the air through the outlet 141, a difference occurs between an air pressure in the vicinity of the first communication hole 34 and an air pressure in the water supply connection portion 41. That is, in the case of injecting only the air through the outlet 141, there is a difference between the air pressure at P1 position near the first communication hole 34 and on the other end side of the joining recessed portion 134 and the air pressure at P2 position near a residual water surface in the water supply connection portion 41. Such a difference in the air pressure leads to a result of sucking up residual water in the water supply connection portion 41 from the water supply connection portion 41, which causes a problem that some water is injected together with the air unlike the user's original intention.

To cope with the problem, in the endoscope 10 according to the first embodiment, the dimension L4 of the second communication hole 44 is substantially equal to the dimension L2 of the first communication hole 34, but the dimension L3 of the second communication hole 44 is shorter than the dimension L1 of the first communication hole 34, as described above. That is, the size of the first communication hole 34 is larger than the size of the second communication hole 44.

Therefore, as compared with a case where the first communication hole 34 and the second communication hole 44 are equal in size, an increase in flow velocity of the air in the vicinity of the first communication hole 34 can be suppressed, and the flow of the air becomes smooth, so that generation of a vortex in the vicinity of the first communication hole 34 can be suppressed. Therefore, it is possible to suppress a decrease in the air pressure in the vicinity of the first communication hole 34, that is, at the P1 position.

Figure 8:
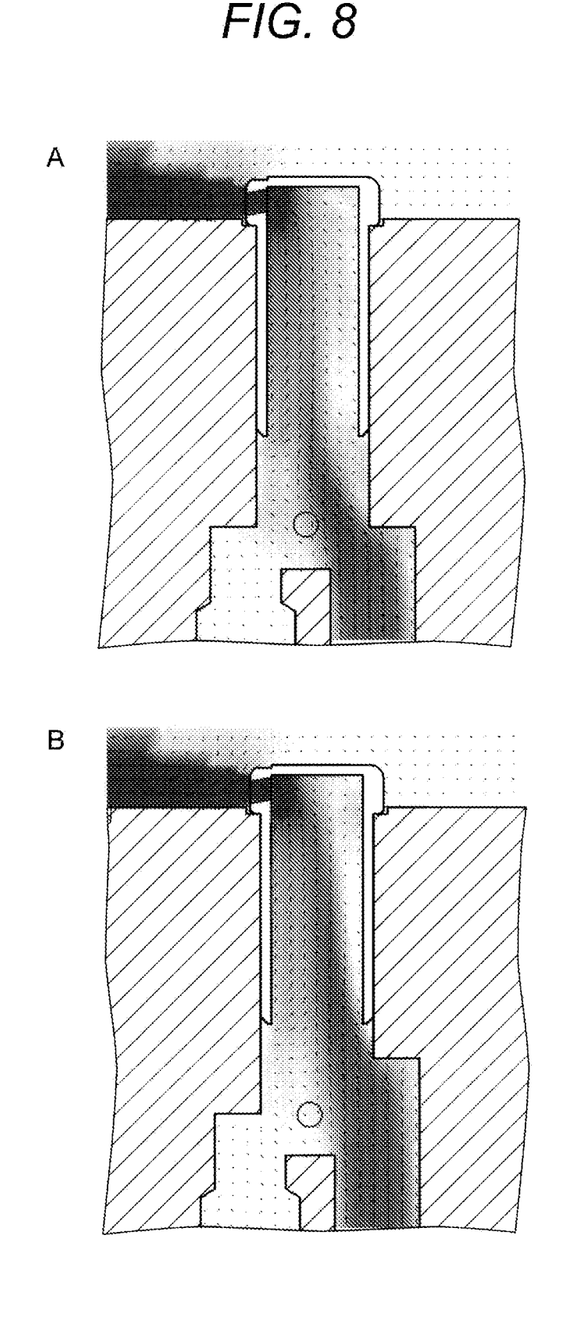
FIG. 8 is simulation results illustrating flow of air in a case where sizes of a first communication hole and a second communication hole are the same and in a case where the size of the first communication hole is larger than the size of the second communication hole.

FIG. 8 is simulation results illustrating flow of air in a case where sizes of the first communication hole 34 and the second communication hole 44 are the same and in a case where the size of the first communication hole 34 is larger than the size of the second communication hole 44. That is, FIG. 8A illustrates a conventional endoscope, and FIG. 8B illustrates the endoscope 10 according to the first embodiment.

Note that, in FIG. 8, a direction of an arrow indicates a flow direction of air, a length of the arrow indicates a speed of the air, and brightness and darkness also indicate a speed of the air.

As can be seen from FIG. 8, the length of the arrow at the P1 position (the o portion in FIG. 8) is shorter in FIG. 8B than in FIG. 8A. That is, the speed of the air at the P1 position is suppressed in FIG. 8B as compared with FIG. 8A.

As described above, the endoscope 10 according to the first embodiment can suppress the speed of the air at the P1 position on the other end side of the joining recessed portion 134, and can suppress the generation of the difference between the air pressure at the P1 position and the air pressure at the P2 position in the vicinity of the residual water surface in the water supply connection portion 41. Therefore, in the case of the air supply operation of injecting only the air through the outlet 141, it is possible to prevent in advance the problem that some water is injected together with air.

Furthermore, in the endoscope 10 according to the first embodiment, the first communication hole 34 has the dimension L1 longer than the dimension L2, and the orthogonal opening portion 341 is wider than the parallel opening portion 342, as described above. Therefore, a ratio of the air flowing into the joining recessed portion 134 through the orthogonal opening portion 341 is larger than a ratio of the air flowing into the joining recessed portion 134 through the parallel opening portion 342.

Therefore, in FIG. 8B, the high-speed portion in the air flow, that is, the portion with high concentration is shifted away from the second communication hole 44 than in FIG. 8A.

That is, the endoscope 10 according to the first embodiment shifts the portion where the air flow is at a high speed away from the second communication hole 44, thereby providing a synergistic effect in suppressing the decrease in the air pressure at the P1 position.

Second Embodiment

Figure 9:
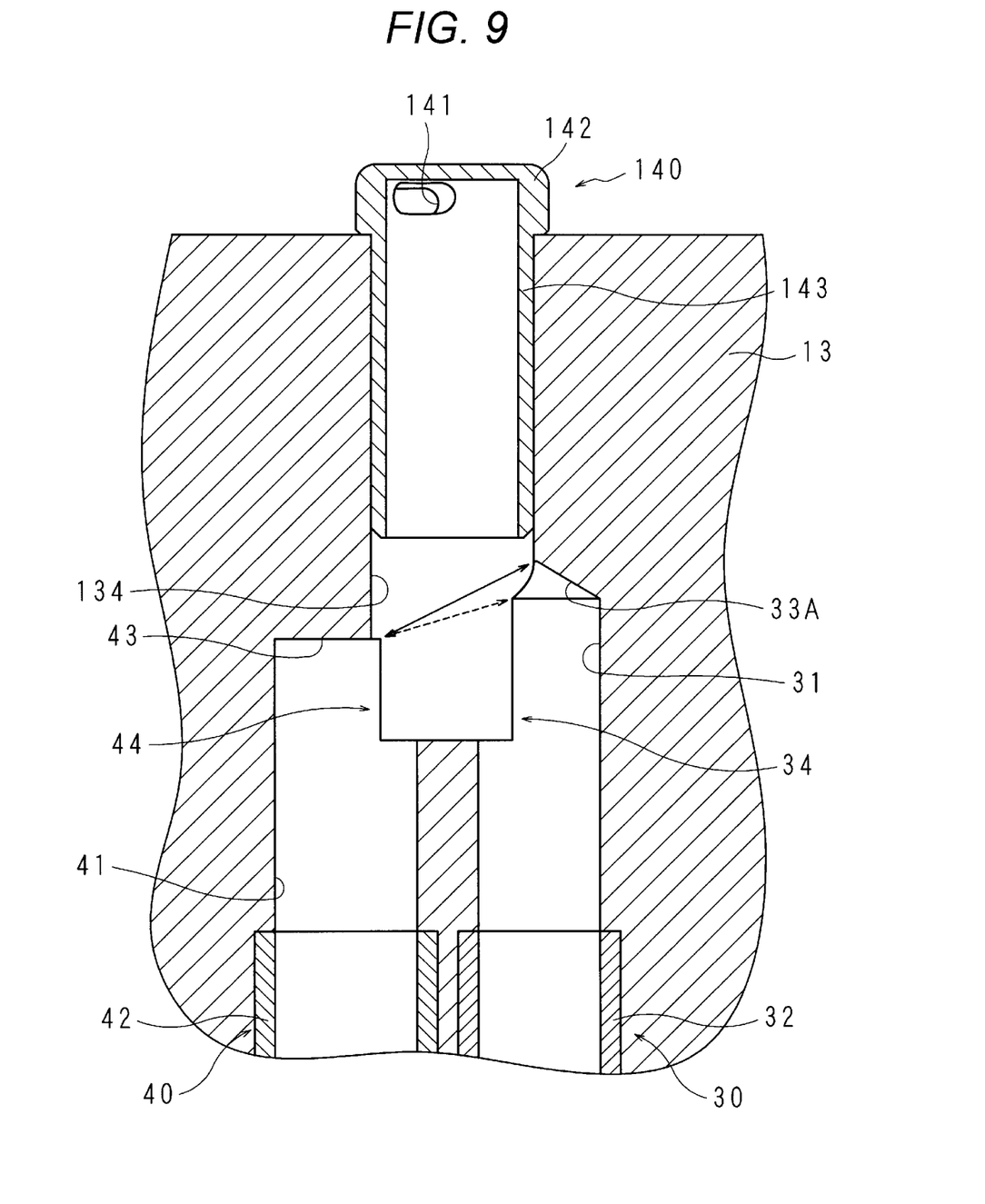
FIG. 9 is an enlarged view illustrating a portion of a joining recessed portion in an enlarged manner of an endoscope according to a second embodiment.

FIG. 9 is an enlarged view illustrating a portion of a joining recessed portion 134 in an enlarged manner of an endoscope 10 according to a second embodiment.

An air supply connection portion 31 has a substantially cylindrical shape, and an upstream end thereof is connected to an air supply tube 32. Further, in the air supply connection portion 31, a gas guide wall 33A for guiding air into a joining recessed portion 134 is formed at a downstream end. The gas guide wall 33A is obliquely formed with respect to an axial length direction of the air supply connection portion 31, and a dimension in a radial direction of the air supply connection portion 31 decreases toward the downstream side of the air supply connection portion 31.

A first communication hole 34 is formed in a communication portion between the air supply connection portion 31 and the joining recessed portion 134. Similarly to the first embodiment, the first communication hole 34 includes an orthogonal opening portion 341 (see FIGS. 5 and 7) opening in a direction orthogonal to the axial length direction of the air supply connection portion 31 and a parallel opening portion 342 (see FIGS. 6 and 7) opening in a direction parallel to the axial length direction of the air supply connection portion 31, and the orthogonal opening portion 341 is wider than the parallel opening portion 342.

A water supply connection portion 41 has a substantially cylindrical shape, and an upstream end thereof is connected to a water supply tube 42. Further, in the water supply connection portion 41, a liquid guide wall 43 for guiding water to the joining recessed portion 134 is formed at a downstream end. The liquid guide wall 43 is formed so as to be orthogonal to the axial length direction of the water supply connection portion 41.

A second communication hole 44 is formed in a communication portion between the water supply connection portion 41 and the joining recessed portion 134. Similarly to the first embodiment, the second communication hole 44 includes an orthogonal opening portion (not illustrated) opening in a direction orthogonal to the axial length direction of the water supply connection portion 41 and a parallel opening portion 442 (see FIG. 6) opening in a direction parallel to the axial length direction of the water supply connection portion 41.

As described above, in the endoscope 10 according to the second embodiment, the gas guide wall 33A that guides the air from the air supply tube 32 into the joining recessed portion 134 is obliquely formed with respect to the axial length direction of the air supply connection portion 31, and the liquid guide wall 43 is formed so as to be orthogonal to the axial length direction of the water supply connection portion 41.

Therefore, the air smoothly flows in the vicinity of the first communication hole 34 without rapidly changing its direction. Therefore, generation of a vortex can be suppressed, and a high-speed portion of air flow in the vicinity of the first communication hole 34 can be shifted to the vicinity of the first communication hole 34 further away from the second communication hole 44. As a result, since the flow of air is reduced at P1 position (see FIG. 4), it is possible to suppress generation of a difference in air pressure between the P1 position and P2 position, and it is possible to prevent in advance a problem that some water is injected together with air in a case of an air supply operation.

Furthermore, in the second embodiment, a distance between the gas guide wall 33A and the liquid guide wall 43 (see the solid arrow in FIG. 9) is longer than a distance between the gas guide wall 33A and the liquid guide wall 43 (see the broken arrow in FIG. 9) in a case where the gas guide wall 33A is provided to be orthogonal to the axial length direction of the air supply connection portion 31. Therefore, the high-speed portion of the flow of air is distant from the water supply connection portion 41 in the vicinity of the first communication hole 34, and residual water in the water supply connection portion 41 is less easily affected by the above-described difference in air pressure.

Portions similar to those in the first embodiment are denoted by the same reference numerals, and detailed descriptions thereof are omitted.

Third Embodiment

Figure 10:
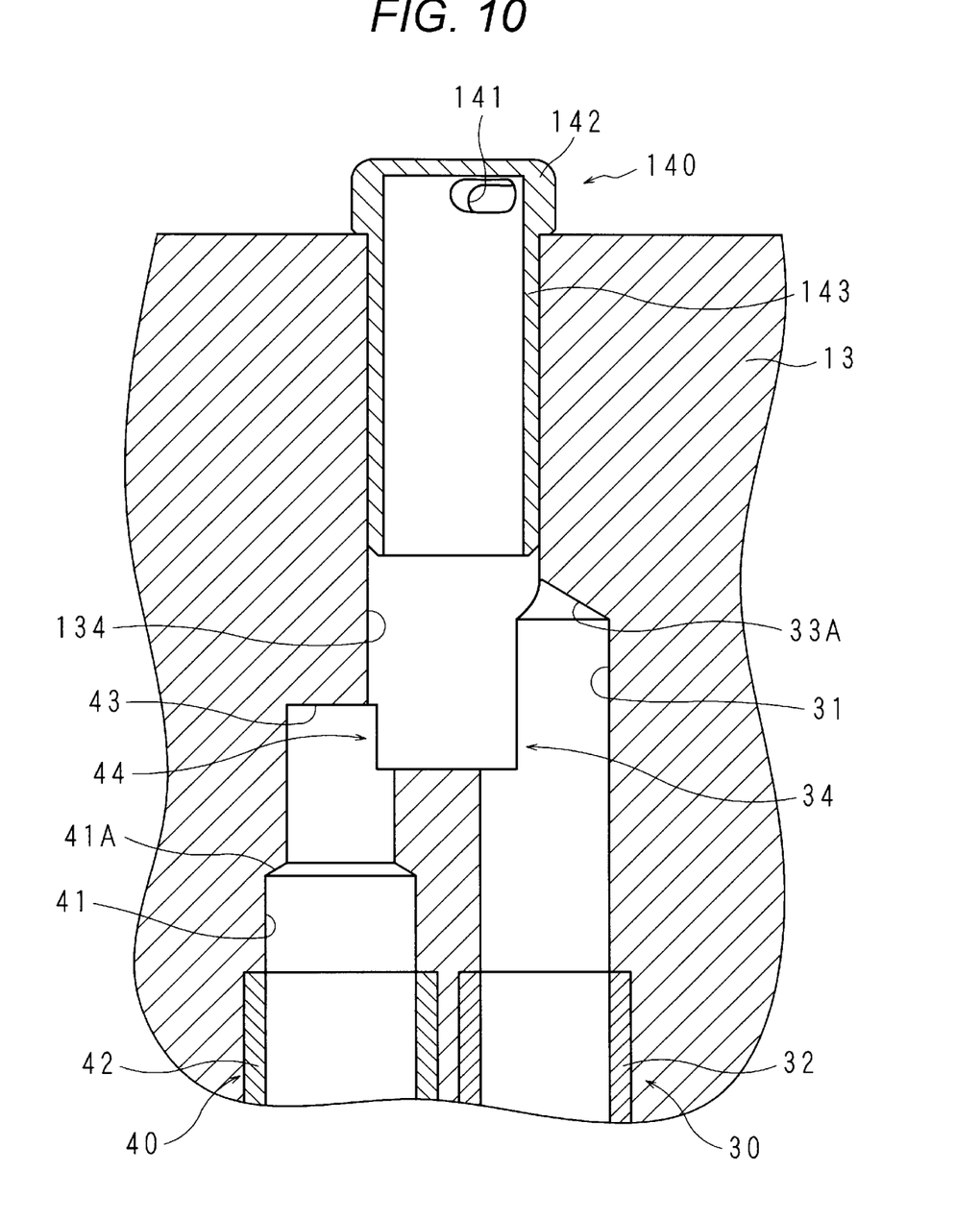
FIG. 10 is an enlarged view illustrating a portion of a joining recessed portion in an enlarged manner of an endoscope according to a third embodiment.

FIG. 10 is an enlarged view illustrating a portion of a joining recessed portion 134 in an enlarged manner of an endoscope 10 according to a third embodiment.

An air supply connection portion 31 has a substantially cylindrical shape, and an upstream end thereof is connected to an air supply tube 32. Further, in the air supply connection portion 31, a gas guide wall 33A for guiding air into a joining recessed portion 134 is formed at a downstream end. The gas guide wall 33A is obliquely formed with respect to an axial length direction of the air supply connection portion 31.

A first communication hole 34 is formed in a communication portion between the air supply connection portion 31 and the joining recessed portion 134. The shape of the first communication hole 34 is similar to that of the first embodiment, and a detailed description thereof will be omitted.

A water supply connection portion 41 has a substantially cylindrical shape, and an upstream end thereof is connected to a water supply tube 42. Further, in the water supply connection portion 41, a liquid guide wall 43 for guiding water to the joining recessed portion 134 is formed at a downstream end. The liquid guide wall 43 is formed so as to be orthogonal to the axial length direction of the water supply connection portion 41.

Furthermore, in the water supply connection portion 41, a diameter-reduced portion 41A with a diameter gradually reduced toward a downstream side is formed in an intermediate part in the axial length direction, and an upstream side of the diameter-reduced portion 41A is larger in diameter than a downstream side of the diameter-reduced portion 41A.

A second communication hole 44 is formed in a communication portion between the water supply connection portion 41 and the joining recessed portion 134. The shape of the second communication hole 44 is similar to that of the first embodiment, and a detailed description thereof will be omitted.

As described above, in the endoscope 10 according to the third embodiment, the diameter-reduced portion 41A is formed in the water supply connection portion 41, and the diameter on the downstream side of the diameter-reduced portion 41A is smaller than the diameter on the upstream side. That is, since the diameter on the downstream side of the water supply connection portion 41 is small, surface tension of residual water in the water supply connection portion 41 increases, and the residual water in the water supply connection portion 41 is less easily affected by a difference in air pressure generated between P1 position and P2 position (see FIG. 4). Therefore, even in the case where the difference in air pressure is generated between the P1 position and the P2 position, suction of the residual water in the water supply connection portion 41 is suppressed.

In the above description, the case where the liquid guide wall 43 is formed to be orthogonal to the axial length direction of the water supply connection portion 41 has been described as an example, but the embodiment is not limited thereto. For example, the liquid guide wall 43 may be obliquely formed with respect to the axial length direction of the water supply connection portion 41, similarly to the gas guide wall 33A.

Portions similar to those in the first embodiment are denoted by the same reference numerals, and detailed descriptions thereof are omitted.

Technical features (constitutional requirements) that have been described in the first to third embodiments can be combined with one another, and a new technical feature can be formed with the combination.

The embodiments that have been disclosed herein should be considered to be illustrative and not restrictive in all respects. The scope of the present invention is indicated by the scope of claims, not the above-described meaning, and is intended to include all modifications within the meaning and scope equivalent to the claims.

REFERENCE SIGNS LIST

10 Endoscope
13 Distal end portion
14 Insertion portion
30 Gas path
31 Air supply connection portion
33 Gas guide wall
34 First communication hole
40 Liquid path
41 Water supply connection portion
41A Diameter-reduced portion
43 Liquid guide wall
44 Second communication hole
134 Joining recessed portion
140 Air supply/water supply nozzle

The invention claimed is:
1. An endoscope comprising;
a liquid path extending along a liquid path axis and through which a liquid passes;
a gas path extending along a gas path axis and through which a gas passes, the liquid path axis and the gas path axis extending parallel to and being different from each other;
a joining recessed portion extending along a joining axis and in which the liquid and the gas join formed in a distal end portion of the endoscope, the joining axis, the liquid path axis and the gas path axis extending parallel to and being different from each other; and
a gas guide wall obliquely formed with respect to an axial length direction of the gas path, wherein
one end side of the liquid path and one end side of the gas path communicate with the joining recessed portion,
a first communication hole is formed at an intersection between the gas path and the joining recessed portion, and a second communication hole is formed at an intersection between the liquid path and the joining recessed portion,
a size of the first communication hole is larger than a size of the second communication hole, and
the gas guide wall is formed on the one end side of the gas path and guides the gas to the first communication hole.
2. The endoscope according to claim 1, wherein a dimension in an axial length direction of the gas path is longer than a dimension in a direction intersecting the axial length direction of the gas path in the first communication hole.
3. The endoscope according to claim 1, wherein
a liquid guide wall that guides the liquid to the second communication hole is formed on the one end side of the liquid path, and
the liquid guide wall is perpendicularly formed with respect to an axial length direction of the liquid path.
4. An endoscope comprising;
a liquid path extending along a liquid path axis and through which a liquid passes;
a gas path extending along a gas path axis and through which a gas passes, the liquid path axis and the gas path axis extending parallel to and being different from each other;
a joining recessed portion extending along a joining axis and in which the liquid and the gas join formed in a distal end portion of the endoscope, the joining axis, the liquid path axis and the gas path axis extending parallel to and being different from each other, wherein
one end side of the liquid path and one end side of the gas path communicate with the joining recessed portion,
a first communication hole is formed at an intersection between the gas path and the joining recessed portion, and a second communication hole is formed at an intersection between the liquid path and the joining recessed portion,
a size of the first communication hole is larger than a size of the second communication hole, and
the liquid path has a cylindrical shape, and further includes a diameter-reduced portion on the one end side.
5. The endoscope according to claim 4, wherein a dimension in an axial length direction of the gas path is longer than a dimension in a direction intersecting the axial length direction of the gas path in the first communication hole.
6. The endoscope according to claim 4, wherein
a gas guide wall that guides the gas to the first communication hole is formed on the one end side of the gas path, and
the gas guide wall is obliquely formed with respect to an axial length direction of the gas path.

7. The endoscope according to claim 4, wherein
a liquid guide wall that guides the liquid to the second communication hole is formed on the one end side of the liquid path, and
the liquid guide wall is perpendicularly formed with respect to an axial length direction of the liquid path.

\* \* \* \* \*